(12) United States Patent
Abbitt et al.

(10) Patent No.: US 6,797,859 B2
(45) Date of Patent: Sep. 28, 2004

(54) VASCULAR TISSUE PREFERRED PROMOTERS

(75) Inventors: Shane E. Abbitt, Ankeny, IA (US); Chun Ping Li, Johnston, IA (US); Xiaomu Niu, Johnston, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 10/195,781

(22) Filed: Jul. 15, 2002

(65) Prior Publication Data

US 2003/0106088 A1 Jun. 5, 2003

Related U.S. Application Data

(60) Provisional application No. 60/305,362, filed on Jul. 13, 2001.

(51) Int. Cl.$^7$ .......................... C12N 15/09; C12N 15/82; A01H 5/00; A01H 5/10
(52) U.S. Cl. ........................ 800/287; 800/278; 800/279; 800/295; 800/320; 800/317; 435/468; 435/419; 435/320.1; 536/24.1
(58) Field of Search ................................ 800/278, 287, 800/279, 295, 317, 320, 298, 301; 435/468, 320.1, 419; 536/24.1, 23.6, 23.71, 23.72

(56) References Cited

U.S. PATENT DOCUMENTS

| | | | |
|---|---|---|---|
| 5,495,007 A | * | 2/1996 | Thompson et al. |
| 5,604,121 A | * | 2/1997 | Hilder et al. ............. 435/172.3 |
| 5,981,835 A | | 11/1999 | Austin-Phillips et al. |
| 2002/0040490 A1 | | 4/2002 | Genetics |

FOREIGN PATENT DOCUMENTS

WO   WO 98/16651   4/1998

OTHER PUBLICATIONS

Stadler et al. Phloem Loading by the PmSUC2 Sucrose Carrier from Plantago Major Occurs into Companion Cells. The Plant Cell (1995), vol. 7, pp. 1545–1554.*
Martin et a. Expression of an Arabidopsis Sucrose Synthase Gene Indicates a Role in Metabolization of Sucrose Both during Phloem loading and in Sink Organs. The Plant Journal (1993), vol. 4, pp. 367–377.*
Riesmeier et al. Evidence of an Essential Role of the Sucrose Transporter in Phloem Loading and Assimilate Partitioning. The EMBO Journal (1994), vol. 13 (1), pp. 1–7.*
Truenit et al. The Promoter of the *Arabidopsis thaliana* SUC2 Sucrose–H+ Syymporter gene directs expression of B–glucuronidase to the Phloem: Evidence for Phloem Loading and Unloading by SUC2. Planta (1995), vol. 196, pp. 564–570.*
Kim et al. Plant Molecular Biology, vol. 24, pp. 105–117, 1994.*
Benfey et al. Science, vol. 250, pp. 959–966, 1990.*
Keller et al. The Plant Cell, vol. 3, pp. 1051–1061, 1991.*
Yang et al. PNAS, vol. 87, pp. 4144–4148, 1990.*
Benfey, et al., "The Cauliflower Mosaic Virus 35S Promoter: Combinatorial REgulation of Transcription in Plants", Science, vol. 250, pp. 959–966, Nov. 16, 1990.
Keller, et al., "Vascular–Specific Expression of the Bean GRP 1.8 Gene is Negatively Regulated", The Plant Cell, vol. 3, pp. 1051–1061, Oct. 1991.
Kim, et al., "A 20 nucleotide upstream element is essential for nopaline synthase (nos) promoter activity", Plant Molecular Biology, 24:105–117, 1994.
Yang, et al., "Maize sucrose synthase–1 promoter directs phloem cell–specific expression of Gus gene in transgenic tobacco plants", Proc. Natl. Acad. Sci USA, vol. 87, pp. 4144–4148, Jun. 1990.
Blewitt, et al., "ESTs from developing cotton fiber", Unpublished, Reference No. A1729894.
Taylor, et al., "The irregular xylem3 locus of arabidopsis encodes a cellulose synthase required for secondary cell wall synthesis", The Plant Cell, vol. 11, pp. 769–779, May 1999.
Poulton, et al., "Tissue level compartmentation of (R)–amygdalin and amygdalin hydrolase prevents large–scale cyanogenesis in undamaged prunus seeds", Plant Physiol., 104: 29–35, 1994.
Poulton, et al., EMBL/GenBank/DDBJ databases, Reference No. U50201.
Swain, et al., "Immunocytochemical localization of prunasin hydrolase and mandelonitrile lyase in stems and leaves of prunus serotina", Plant Physiol., 106: 1285–1291, 1994.
Vysotskaia, et al., "*Arabidopsis thaliana* chromsome 1 BAC T13D8 sequence", EMBL/GenBank/DDBJ databases, Reference No. AC004473.
Zheng, et al., "Temporal and spatial expression of amygdalin hydolase and (R)–(+)–mandelonitrile lyase in black cherry seeds", Plant Physiol., 109: 31–39, 1995.

* cited by examiner

Primary Examiner—Medina A. Ibrahim
(74) Attorney, Agent, or Firm—Pioneer Hi-Bred International, Inc.

(57) ABSTRACT

The present invention provides compositions and methods for regulating expression of heterologous nucleotide sequences in a plant. Compositions include a novel nucleotide sequence for a vascular tissue-preferred promoter for the gene encoding prunasin hydrolase and sequences isolated therefrom. A method for expressing a heterologous nucleotide sequence in a plant using the promoter sequences disclosed herein is provided. The method comprises stably incorporating into the genome of a plant cell a nucleotide sequence operably linked to the vascular tissue-preferred promoter of the present invention and regenerating a stably transformed plant that expresses the nucleotide sequence.

19 Claims, 6 Drawing Sheets tggggtgcttacacccacaatcatccaggtctacttattttctccaaatccttttatggtttcaactagtcagtgcccti
tgctctcacaattaagtccacatatgtggactacagtaattaaacatatggttttcaatgtctaaacaagccaatac
ttcatggatttgagttatgcatggcataccgttctgttttaagtgttattaaagtgcctgcaaggaattcttacaaggat
acaattctatactaataccaatacaagataacataacaaaatactaattcgctctgacatcaatggcacacaat
gaggtgacaagtttccgagaaagttagagaaaatgttacttgcattctccaatttaatatctaaatagctaaattac
tttgtgcttttaattactaatagtcatgtaatatgtatatttggtctacagacatacacgcacacactagtttacatgatct
gatttcccaaactttatgcttaaataaaaataatctttggttaattgcgagagaaatttgttttgagcaattaatgccaa
ttgatggagataggagagaaaacattaatggagaagggtgcaattagattatctttccaaaaccagaggttagg
gcacgggagcaaaaccagactctgaaggtgatcccaatggaatctttggattgcttttccatactttagctttaaa
gccctgcttggctttacaaaaaagaaagcaaaaaagaaagcaaaatgcttttgatttattattttcacgtgtaga
agttatgtactccttctatataaatcccatgcaatatagcaggaagagcacacctagctcgatcataaaaaatcct
ccactgagcc

FIGURE 1

```
                         1                                                50
PH DL1.4 PRO       (1)   --------------------------------------------------
PH DL1.1 PRO       (1)   GATACCGTGCGAAAGGTCTTCTTGGCCCTTGGAGATTGACACCTAATCAG
Consensus          (1)
                         51                                               100
PH DL1.4 PRO       (1)   --------------------------------------------------
PH DL1.1 PRO      (51)   AATTTTGATAAAGTTAAATGTATCTAAAAAGTAATCCCTTTTCTTTTCTT
Consensus         (51)
                         101                                              150
PH DL1.4 PRO       (1)   --------------------------------------------------
PH DL1.1 PRO     (101)   TTTTCATCTATAATAGCAAACGAATAAATACTATAGACACAGACCTAAAT
Consensus        (101)
                         151                                              200
PH DL1.4 PRO       (1)   ---TGGGGTGCTTACACCCACAATCATCCAGGTCTAC-TTATTTTGTCCA
PH DL1.1 PRO     (151)   ATTTGAAGCACATGTAAGAACAGGGCGC-AGCCAAACGTTTTCTTCAACA
Consensus        (151)       TG  G  CT  A C ACA     C AG   AC TT T TTC  CA
                         201                                              250
PH DL1.4 PRO      (47)   AATCCTTT--T---ATGGTTTCAACTA-GTCAGTGCCC--------TTTG
PH DL1.1 PRO     (200)   TATTAGTTTTTTTCAATTGTGTCAAATAAGTCGGTATGAAAGAAAATTCTG
Consensus        (201)    AT    TT  T    AT GT TCAA TA GTC GT         T TG
                         251                                              300
PH DL1.4 PRO      (83)   CTCTCACAATTAAGTGCACATATGTCGACTACAGTAATTAAACATA--TG
PH DL1.1 PRO     (250)   AGATAAAGATTGGTGCAGCATAAATGGACTTTTGAAAAAAAAAAAAATTG
Consensus        (251)     T A ATT   C  CATA  TGGACT   G AA  AAA A A  TG
                         301                                              350
PH DL1.4 PRO     (131)   GT-------TTTCAATGTCTAA------ACAAGCCA--ATACTTCATGGATT
PH DL1.1 PRO     (300)   ATCCCCCCTCTCTAGGTCTTGGTGTCGAAAGCCATAAAAATTGATCCCCC
Consensus        (301)    T        T TC A GTCT         AAGCCA   A A TT AT
                         351                                              400
PH DL1.4 PRO     (168)   TGAGTTATGCATGGCA-TACGGTTCTG---TTTTAAGTGTTATTAAAGTG
PH DL1.1 PRO     (350)   CCTCTTTTCCCTATAACTCCCCTTCCCCCCTCTTTAGGTTTTTTTAAAGTT
Consensus        (351)      TT T C T   A  CC TTC      T TT AG  TT TTAAAGT
                         401                                              450
PH DL1.4 PRO     (214)   ---C--------CTGCAAGGAAT-------TCTTA-------CAAGGATA
PH DL1.1 PRO     (400)   AAACAGAGATCACAGAGTGGAATCACCTTCTCTTTATTGGGGCTTGGGGT
Consensus        (401)      C        C G   GGAAT       TCTT        C  GG
                         451                                              500
PH DL1.4 PRO     (239)   CAATTCTATACT------AATA--CCAATACAAGATAACATAAG------
PH DL1.1 PRO     (450)   CGGATGGATAGGTGAGGGAGTAGGCGGGTGCGGGTGAAGCTGGCCGTGGG
Consensus        (451)   C  T ATA       A TA     C   T C G  AA  T  C
                         501                                              550
PH DL1.4 PRO     (275)   ----AAAATACTAATTCGCTCTGACATCAATGGCACACAATGAGGTGACA
PH DL1.1 PRO     (500)   GTTTAAGCTACTCCTTTTTCAATTTAAAAWAWGAWTTCYAWTACCTTGSA
Consensus        (501)       AA  TACT TT           A  A    G   CAA T    A
                         551                                              600
PH DL1.4 PRO     (321)   AGTTTCCGAGAAAGTTAGAGAAAAATGTTACTTGCATTCTCCAATTTAATA
PH DL1.1 PRO     (550)   ACCTTAATATTATTTTTKTGCMAAAGGKACTTWAMACAATTATTCTATAG
Consensus        (551)   A  TT   A  A  TT  G  AA G  ACTT          A T TA
                         601                                              650
PH DL1.4 PRO     (371)   TCTAAATAGCTAAATTAC--TTTGTGCTTTTAATTACTAATAGTCATGTA
PH DL1.1 PRO     (600)   TAAAAGTTGTCCAAGGCCCGTATGTACATGAGAGGACGTGTTGAGAGTAG
Consensus        (601)   T  AA T G   AA    C   T TGT C T   A  AC  TG A
```

FIGURE 2(a)

```
                         651                                            700
PH DL1.4 PRO    (419)    ATATGTATATTTGGTC---TACACAGATA------CACGCACACACTAGT
PH DL1.1 PRO    (650)    ATAT-TATGTTAAGTCCATATATACGTGAGAGGGCATGTTGAAAGTAGA
   Consensus    (651)    ATAT TAT TT  GTC    TA A AC T        CA G    A A TAG
                         701                                            750
PH DL1.4 PRO    (460)    TTACATGATCTGATTTCCCAA-ACTT------TATGCTTAAA-TAAAAA
PH DL1.1 PRO    (699)    TATTATGTTAAGTTTTGTATATACGTGAGAGGCATATGTTGAGAGTAAATA
   Consensus    (701)    T   ATG T  G TTT     A AC T         TATG T A A TAAA A
                         751                                            800
PH DL1.4 PRO    (501)    TAATCTT-----TGGTTAATTGCGAG---AGAAATTTGTTTTCAGCAATT
PH DL1.1 PRO    (749)    TTATGTTAAGTCTGTTTTTTTTTAAATGAAGTAATTGTTTTTAGCAATT
   Consensus    (751)    T AT TT      TG TT  TT   A     AG AATTTGTTTT AGCAATT
                         801                                            850
PH DL1.4 PRO    (543)    AATGCCAATTGATGGACATAGGAGAGAAAACATTAATGGACAAGGGTGCA
PH DL1.1 PRO    (799)    AACAGCAATTGATGGAAATAGGAGAGAAAACATTAATGGAGAAGGATGCA
   Consensus    (801)    AA  CCAATTGATGGA ATAGGAGAGAAAACATTAATGGAGAAGG TGCA
                         851                                            900
PH DL1.4 PRO    (593)    ATTGATTATCTTTCCAAAACCAGAGGTTAGGGCACGGGAGCAAAACCAG
PH DL1.1 PRO    (849)    ATTAGATTATCTTTCCAAAACCAAGGTTAGGGCACGGGAGCAAAACCAG
   Consensus    (851)    ATTAGATTATCTTTCCAAAACCA AGGTTAGGGCACGGGAGCAAAACCAG
                         901                                            950
PH DL1.4 PRO    (643)    ACTCTGAAGGTGATCCCAATGGAATCTTTGGATTGCTTTTC---------
PH DL1.1 PRO    (899)    ACTCTGAAGGTAGTCCCAGTGGATCTTTGGATTGCTTTCTATAAAGTA
   Consensus    (901)    ACTCTGAAGGT  TCCCA TGG ATCTTTGGATTGCTTTC
                         951                                            1000
PH DL1.4 PRO    (684)    --------------------------------------------------
PH DL1.1 PRO    (949)    GTATATAAAGAAGGATCTTTGGGTTACTTGTCTGATATTTTTCCGAAACA
   Consensus    (951)
                         1001                                           1050
PH DL1.4 PRO    (684)    --------------------------------------------------
PH DL1.1 PRO    (999)    ACCCACCAACATTTTTACTATATGCATGCAGGACCCTACTTTTCTCTGTC
   Consensus    (1001)
                         1051                                           1100
PH DL1.4 PRO    (684)    -----C-ATACTTTAGCTT---------------------------T
PH DL1.1 PRO    (1049)   TGTACCCATACTTTAGCTTCTTCTTTTTTTGTGGTTATCCGTACTTTAGT
   Consensus    (1051)        C ATACTTTAGCTT                                T
                         1101                                           1150
PH DL1.4 PRO    (698)    A--AAGCTTCTGCTTGGCTTTACAAAAAGAAAGCAAAAAAGAAAGCAAA
PH DL1.1 PRO    (1099)   TTTAAGGCCC-GCTTGGCTTTACAAAAAGAAAGCAAAAAAGACATAAAA
   Consensus    (1101)      AAG CCC GCTTGGCTTTACAAAAAGAAAGCAAAAAAGA A   AAA
                         1151                                           1200
PH DL1.4 PRO    (746)    ATGCTTTTTGATTTATTATTTTCACGTGTAGAAGTTATGTACTCCTTCTAT
PH DL1.1 PRO    (1148)   ACTTCTCTGATTTATTATTTTCAGGTGCAGAAGTTACGTACTCCCTCTAT
   Consensus    (1151)   A     T TGATTTATTATTTTCA GTG AGAAGTTA GTACTCC TCTAT
                         1201                                           1250
PH DL1.4 PRO    (796)    ATAAATCCCATGCAATATAGCAGGAGAGCACCCTAGCTGGATCATAAA
PH DL1.1 PRO    (1198)   ATAAAGCCCATGCAATATAGCAGGAAGAGCAACCTAGCTCGATCACCAA
   Consensus    (1201)   ATAAA CCCATGCAATATAGCAGGAAGAGCA ACCTAGCTCGATCA  AA
                         1251       1267
PH DL1.4 PRO    (846)    AAATCCTCCACTGAGCC
PH DL1.1 PRO    (1248)   AAACCCTCCTCTCAGCC
   Consensus    (1251)   AAA CCTCC CT AGCC
```

FIGURE 2(b)

| Tissue | # events w/ GUS expression | Note |
|---|---|---|
| Leaf blade | 9 out of 10 checked | Vascular bundles and surrounding tissue |
| Midrib | 9 out of 10 checked | Vascular bundles on abaxial side |
| Leaf sheath | 5 out of 5 checked | Spotty |
| Internode | 4 out of 5 checked | Spotty |
| Node | 0 out of 5 checked | |
| Pulvinus | 4 out of 4 checked | Weak |
| Root | 1 out of 5 checked | Weak |
| Tassel | 4 out of 6 checked | In glume outside of anther |
| Ear | 5 out of 5 checked | Maternal tissues (pedicel, glume) |

FIGURE 3

VASCULAR TISSUE PREFERRED PROMOTERS

CROSS-REFERENCE TO RELATED APPLICATIONS

This application claims the benefit of U.S. Provisional Application No. 60/305,362, filed Jul. 13, 2001.

FIELD OF THE INVENTION

The present invention relates to the field of plant molecular biology, more particularly to the regulation of gene expression in plants.

BACKGROUND OF THE INVENTION

Expression of heterologous DNA sequences in a plant host is dependent upon the presence of an operably linked promoter that is functional within the plant host. Choice of the promoter sequence will determine when and where within the organism the heterologous DNA sequence is expressed. Thus, where expression is desired in a preferred tissue of a plant, tissue-preferred promoters are utilized. In contrast, where gene expression throughout the cells of a plant is desired, constitutive promoters are the regulatory element of choice. Additional regulatory sequences upstream and/or downstream from the core promoter sequence may be included in expression constructs of transformation vectors to bring about varying levels of tissue-preferred or constitutive expression of heterologous nucleotide sequences in a transgenic plant.

Frequently it is desirable to have preferential expression of a DNA sequence in a tissue of an organism. For example, increased resistance of a plant to insect attack might be accomplished by genetic manipulation of the plant's genome to comprise a tissue-specific promoter operably linked to a heterologous insecticide gene such that the insect-deterring substances are specifically expressed in the susceptible plant tissues. Preferential expression of the heterologous nucleotide sequence in the appropriate tissue reduces the drain on the plant's resources that occurs when a constitutive promoter initiates transcription of a heterologous nucleotide sequence throughout the cells of the plant.

Alternatively, it might be desirable to inhibit expression of a native DNA sequence within a plant's tissues to achieve a desired phenotype. In this case, such inhibition might be accomplished with transformation of the plant to comprise a tissue-specific promoter operably linked to an antisense nucleotide sequence, such that tissue-specific expression of the antisense sequence produces an RNA transcript that interferes with translation of the mRNA of the native DNA sequence in a subset of the plant's cells.

Phloem tissue transports nutrients, hormones, and other substances throughout the various plant organs. The parenchyma cells of phloem participate in loading and unloading sucrose and other nutrient content into the phloem transport system. The high nutrient content of sap located in phloem tissue causes the phloem to be the target of a variety of insect species, including aphids (family Aphididae), corn borers (family Pyralidae), and leafhoppers (Cicadellidae) among others. Damage to plants resulting from infestation by these insects occurs through multiple mechanisms, including loss of nutrients and water to the insects, introduction of virus particles into the phloem tissue following infestations, and creation of tissue susceptible to fungal attack. A need exists for vascular tissue-preferred promoters operably linked to heterologous nucleotide sequences that help protect a plant against pathogens such as insects, viruses, fungi, nematodes, and the like.

An additional need exists for a vascular tissue-preferred promoter sequence would be operably linked to a heterologous nucleotide sequence that modifies the loading characteristics of vascular tissue and thereby affects plant development and maturation, carbon allocation, and crop yield. By altering the levels of substances involved in phloem loading, the loading characteristics of vascular tissue, plant development and plant growth can be influenced. A need exists for promoter sequences that can be used to modulate expression of substances that regulate vascular tissue loading.

There may also be a use for a vascular tissue-preferred promoter in improvement of stalk strength. For example, via cell wall thickening such as by deposition of more cellulose. A vascular tissue-preferred promoter is desirable to use for expressing genes that are involved in cellulose biosynthesis in order to increase cell wall strength. When cell wall strength is increased in corn stalk, better standability is expected. This is particularly relevant to improving resistance to stalk lodging in corn. An example of such application is to use a vascular tissue-specific promoter to drive a cellulose synthase gene that is involved in secondary cell wall formation, such as the irx3 gene from *Arabidopsis thaliana* (Taylor N G, Scheible W R, Cutler S, Somerville C R, Turner S R. 1999. The irregular xylem3 locus of Arabidopsis encodes a cellulose synthase required for secondary cell wall synthesis. Plant Cell 11:769–80). In this case, cells that do not normally have secondary wall would potentially gain additional cell wall growth, thus leading to a stronger cell structure.

Thus, isolation and characterization of phloem-preferred promoters that can serve as regulatory regions for tissue-preferred expression of heterologous nucleotide sequences of interest are needed for genetic manipulation of plants to exhibit specific phenotypic traits.

SUMMARY OF THE INVENTION

Compositions and methods for regulating expression of heterologous nucleotide sequences in a plant are provided. Compositions comprise novel promoter sequences that initiate transcription in a vascular tissue-preferred manner, particularly a phloem-tissue preferred manner. Specifically a transcriptional initiation region isolated from a *Prunus serotina* gene encoding prunasin hydrolase is provided. Further compositions of the invention comprise the nucleotide sequence set forth in SEQ ID NO.: 1 and a fragment of the nucleotide sequence set forth in SEQ ID NO.: 1. The compositions of the invention further comprise nucleotide sequences having at least 70% identity to the sequence set forth in SEQ ID NO.: 1 or a fragment thereof, and nucleotide sequences that hybridize under stringent conditions to any one of the above-mentioned sequences. The sequence set forth in SEQ ID NO.: 2 represents a modification of the nucleotide sequence made for cloning purposes. The sequence for the prunasin hydrolase operon including the prunasin hydrolase promoter region is set forth in SEQ ID NO.: 3. Nucleotides 989–2626 of SEQ ID NO.: 3 encode a prunasin hydrolase polypeptide. SEQ ID NO.: 4 is the amino acid sequence for the prunasin hydrolase polypeptide. SEQ ID NOS: 5 and 6 are related variations of the polynucleotide sequence disclosed as SEQ ID NO.: 1.

Compositions of the present invention also include a DNA construct comprising a promoter sequence of the invention operably linked to a nucleotide sequence of interest, wherein the promoter is capable of driving expression of the nucleotide sequence in a plant cell. Transformed plant cells, transformed plants, and transformed seeds comprising the novel promoter sequences of the invention are also provided.

Methods for expressing a nucleotide sequence of interest in a plant are provided. The methods comprise stably incorporating into the genome of a plant cell an expression cassette comprising a promoter sequence of the invention operably linked to a nucleotide sequence of interest, wherein the promoter is capable of initiating transcription of the nucleotide sequence in a plant cell. The methods further provide a means for preferentially expressing a nucleotide sequence in vascular tissue, more particularly phloem tissue.

BRIEF DESCRIPTION OF THE DRAWINGS

FIG. 1 depicts the nucleotide sequence of the promoter region of *Prunus serotina* prunasin hydrolase (SEQ ID NO. 13).

FIG. 2 is an alignment and consensus of two genomic fragments SEQ ID NO.: 1 (PH DL1.4 PRO) and SEQ ID NO.: 5 (PH DL1.1 PRO), highlighting related promoter sequence patterns and motifs: TATA box at position 793–796, CAAT signal at 659–662, RGATAOS motif (R-GATA, GATA motif binding factor, required for phloem-specific gene expression of Rice Tungro Bacilliform Virus) binding site at 259–267.

FIG. 3 is a table showing GUS expression in various tissues in transgenic corn plants.

DETAILED DESCRIPTION OF THE INVENTION

Figure 4:
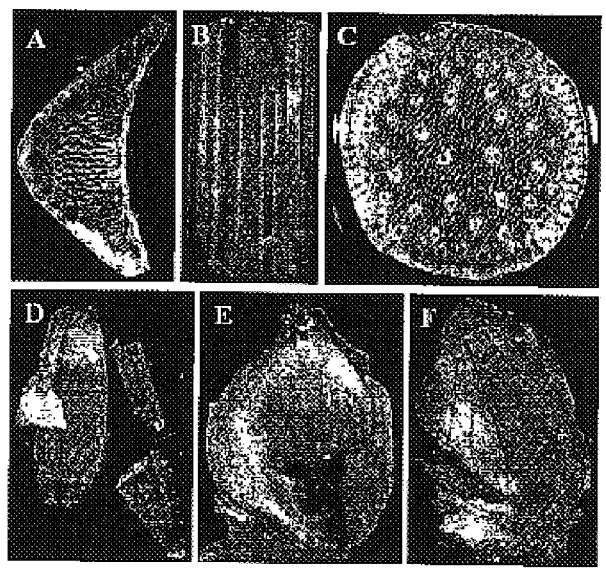
FIG. 4 is GUS expression in Maize TO plants carrying PHP17688. A. 10541640 midrib 60 days; B. 10541657 internode 85 days, longitudinal section (arrow points to GUS expression along a vascular bundle); C. 10541665 internode 85 days, cross section; D. 10541628 anther 60 days; E. 10541665 kernel 4 DAP; F. 10541647 kernel 8 DAP.

Compositions of the invention are nucleic acid molecules comprising a novel nucleotide sequence for a plant promoter for the *Prunus serotina* gene encoding prunasin hydrolase. This promoter sequence confers vascular-tissue preferred expression, more particularly phloem-preferred expression, of an operably linked nucleotide sequence. In particular, the present invention provides for isolated nucleic acid molecules comprising nucleotide sequences encoding the DNA sequence deposited in a bacterial host as Patent Deposit No. PTA-3235, or the nucleotide sequence set forth in SEQ ID NO.: 1, and variants and fragments thereof. This promoter sequence was isolated from the 5'-untranslated region flanking the transcription initiation site of a *P. serotina* gene encoding prunasin hydrolase.

A plasmid containing the *P. serotina* promoter sequence of the invention was deposited with the Patent Depository of the American Type Culture Collection (ATCC), Manassas, Va., on Mar. 27, 2001 and assigned Patent Deposit No. PTA-3235. The last two nucleotides of SEQ ID NO.:1, nucleotides 987 and 988, were altered from C's to T's in the sequence in the plasmid deposited with the ATCC. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The invention encompasses isolated or substantially purified nucleic acid compositions. An "isolated" or "purified" nucleic acid molecule or biologically active portion thereof, is substantially or essentially free from components that normally accompany or interact with the nucleic acid molecule as found in its naturally occurring environment. Thus an isolated or purified nucleic acid molecule, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

By "promoter" or "transcriptional initiation region" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' untranslated region upstream from the particular promoter region identified herein. Thus the promoter region disclosed herein further comprises upstream regulatory elements that confer tissue-preferred expression, particularly vascular tissue-preferred expression, more particularly phloem tissue-preferred expression, yet more particularly phloem parenchyma-preferred expression of any heterologous nucleotide sequence operably linked to the disclosed promoter sequence.

The nucleotide sequences for the promoters of the present invention may be the naturally occurring sequences or any sequence having substantial homology. By "substantial homology" is intended a sequence exhibiting substantial functional and structural equivalence with the native or naturally occurring sequence. Any functional or structural differences between substantially homologous sequences do not affect the ability of the sequence to function as a promoter as disclosed in the present invention. Thus, any sequence having substantial sequence homology with the sequence of a particular promoter of the present invention will direct expression of an operably linked heterologous nucleotide sequence. Two promoter nucleotide sequences are considered substantially homologous when they have at least about 50%, 60%, to 70%, generally about 80%, preferably about 85%, 90%, up to 98% sequence homology.

The isolated promoter sequences of the present invention are characterized as providing for tissue-preferred expression of a nucleotide sequence of interest. The vascular system of plants comprises multiple tissues including xylem and phloem. Phloem tissues comprise numerous cell types including sieve elements or sieve tube members, sieve cells, companion cells (in angiosperms), albuminous cells (in gymnosperms), phloem parenchyma cells, and phloem fibers. The tissue-preferred promoter disclosed herein is capable of preferentially activating transcription of one or more DNA sequences in the vascular system of plants, particularly in phloem tissue, more particularly in phloem parenchyma cells. A nucleotide sequence operably linked to the phloem-preferred promoter disclosed herein results in expression of the operably linked sequence at levels that are higher in vascular tissue, particularly phloem tissue, than in other tissues or than would have been found in the vascular tissue of the untransformed plant.

Fragments and variants of the promoter nucleotide sequence disclosed herein are also encompassed by the present invention. By "fragment" is intended a portion of the nucleotide sequence. Fragments of a nucleotide sequence may retain biological activity and hence initiate transcription of a heterologous nucleotide sequence. Alternatively, fragments of a promoter nucleotide sequence that are useful as hybridization probes generally do not retain biological activity. Thus, fragments of a nucleotide sequence may range from at least about 20 nucleotides, about 50 nucleotides, about 100 nucleotides, and up to the full-length nucleotide sequence of the invention.

Thus, a fragment of a promoter nucleotide sequence may encode a biologically active portion of the promoter, or it may be a fragment that can be used as a hybridization probe or PCR primer using methods disclosed below. A biologically active portion of a promoter can be prepared by isolating a portion of one of the promoter sequences of the invention and assessing the activity of the portion of the promoter. Nucleic acid molecules that are fragments of a promoter nucleotide sequence comprise at least 30, 35, 40, 45, 50, 75, 100, 325, 350, 375, 400, 425, 450, 500, 550, 600, 650, 700, 800, 900, or 988 nucleotides for SEQ ID NO.:1.

The nucleotides of such fragments comprise the TATA recognition sequence of the particular promoter sequence or regulatory elements that confer tissue specificity. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al. (1987) *Methods Enzymol.* 155:335–350, and Erlich, ed. (1989) *PCR Technology* (Stockton Press, New York). Variants of these promoter fragments, such as those resulting from site-directed mutagenesis, are encompassed by the compositions of the present invention.

By "variants" is intended substantially similar sequences. For nucleotide sequences naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least about 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters. Variant nucleotide sequences of the present invention retain biological activity (i.e. regulate transcription). Methods to assay transcriptional regulation are well known in the art. Assay methods include Northern blots, RT-PCR, and use of reporter sequences such as GUS.

Variant nucleotide sequences also encompass sequences derived from a mutagenic and recombinogenic procedure such as DNA shuffling. With such a procedure, one or more different sequences can be manipulated to create a new promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The *P. serotina* promoter sequence of the invention can be used to isolate corresponding sequences from other organisms, particularly other plants, more particularly other dicotyledonous plants. In this manner, methods such as PCR, hybridization, and the like can be used to identify such sequences based on their sequence homology to the sequence set forth herein. Sequences isolated based on their sequence identity to the entire promoter sequence set forth herein or to fragments thereof are encompassed by the present invention. An embodiment of the invention comprises a nucleotide sequence natively associated with and capable of driving expression of a nucleotide sequence that encodes a polypeptide, said polypeptide having at least 74%, 80%, 85%, 90%, 91%, 92%, 93%, 94%, 95%, 96%, 97%, 98%, or 99% sequence identity to the coding sequence of *P. serotina* prunasin hydrolase (Genbank Acc. No. U50201). By "natively associated" is intended that the promoter sequence has not been operably linked to the nucleotide sequence by human intervention. Another embodiment of the invention includes a method for identifying vascular tissue-preferred promoters in the 5' UAS region of nucleotide sequences encoding polypeptides having at least 74%, 80%, 85%, 90%, 91%, 92%, 93%, 94%, 95%, 96%, 97%, 98%, or 99% identity to *P. serotina* prunasin hydrolase (Genbank Acc. No. U50201).

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire promoter sequence disclosed herein, or one or more portions thereof, may be used as a probe capable of specifically hybridizing to corresponding promoter sequences. To achieve specific hybridization under a variety of conditions, such probes include sequences that are unique among promoter sequences and are preferably at least about 10 nucleotides in length, and most preferably at least about 20 nucleotides in length. Such probes may be used to amplify corresponding promoter sequences from a chosen plant by PCR. This technique may be used to isolate additional promoter sequences from a desired plant or as a diagnostic assay to determine the presence of promoter sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m$=81.5° C.+16.6 (log M)+0.41 (%GC) −0.61 (% form) −500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that have promoter activity and which hybridize under stringent conditions to the promoter sequence disclosed herein, or to fragments thereof, are encompassed by the present invention. Such sequences will be at least about 40% to 50% homologous, about 60%, 65%, or 70% homologous, and even at least about 75%, 80%, 85%, 90%, 91%, 92%, 93%, 94%, 95%, 96%, 97%, 98%, 99% or more homologous with the disclosed sequence. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99% or more sequence identity.

The following terms are used to describe the sequence relationships between two or more nucleic acids: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence, for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art.

Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The promoter sequence disclosed in the present invention, as well as variants and fragments thereof, is useful in the genetic manipulation of any plant when assembled within a DNA construct such that the promoter sequence is operably linked with a heterologous nucleotide sequence of interest. The cassette will include 5' and 3' regulatory sequences operably linked to a heterologous nucleotide sequence. By "operably linked" is intended a functional linkage between a promoter sequence of the invention and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. In this manner, the promoter nucleotide sequence is provided in expression cassettes along with heterologous nucleotide sequences for expression in a plant of interest. Such an expression cassette is provided with a plurality of restriction sites for insertion of the heterologous nucleotide sequence to be under the transcriptional regulation of the regulatory regions comprising the promoter sequence of the invention. The cassette may additionally contain at least one additional gene to be cotransformed into the organism. Alternatively, the additional gene(s) can be provided on multiple expression cassettes.

The expression cassette may additionally contain selectable marker genes. Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference. The above list of selectable marker genes is not meant to be limiting. Any selectable marker gene can be used in the present invention.

The expression cassette will include in the 5'-3' direction of transcription, a promoter sequence of the invention, a translational initiation region, a heterologous nucleotide sequence, and a transcriptional and translational termination region functional in plants. The heterologous nucleotide sequence may be native or analogous or foreign or heterologous to the plant host. Additionally, the heterologous nucleotide sequence may be the natural sequence or alternatively a synthetic sequence. By "foreign" is intended that the transcriptional initiation region is not found in the native plant into which the transcriptional initiation region is introduced. As used herein, a chimeric gene comprises a promoter sequence operably linked to a coding sequence that is heterologous to the promoter sequence.

The termination region may be native with the promoter sequence of the invention, may be native with the operably linked heterologous nucleotide sequence, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Where appropriate, the heterologous nucleotide sequences may be optimized for increased expression in the transformed plant. That is, the genes can be synthesized using plant-preferred codons for improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct or expression vector. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV) (Lommel et al. (1991) *Virology* 81:382–385). See also, Della-Cioppa et al. (1987) *Plant Physiol.* 84:965–968.

Other methods known to enhance translation can also be utilized, for example, introns, and the like.

It is recognized that the promoter sequences of the invention may be used to initiate transcription of antisense constructions, complementary to at least a portion of the messenger RNA (mRNA) for the nucleotide sequence of a gene of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence similarity to the corresponding antisensed sequences may be used. Furthermore, portions of the antisense nucleotides may be used to disrupt the expression of target genes. Generally, sequences of at least 50 nucleotides, 100 nucleotides, 200 nucleotides, or greater may be used.

The promoter sequences of the present invention may also be used to initiate transcription of a nucleotide sequence in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See U.S. Pat. Nos. 5,283,184 and 5,034,323; herein incorporated by reference.

The promoter sequences of the present invention are useful in the tissue-preferred expression of a heterologous nucleotide sequence of interest. By "heterologous nucleotide sequence" is intended a sequence that is not naturally occurring with the promoter sequence. While this nucleotide sequence is heterologous to the promoter sequence, it may be homologous or native or heterologous or foreign to the plant host. The heterologous nucleotide sequence operably linked to one of the promoters disclosed herein may encode a polypeptide of interest. Examples of such heterologous genes include, but are not limited to, nucleotide sequences encoding polypeptides conferring resistance to abiotic stress, such as drought, temperature, salinity, ozone, and toxins such as pesticides and herbicides, or to biotic stress, such as attacks by pathogens including insects, viruses, bacteria, fungi, and nematodes, and development of diseases associated with these organisms.

The promoter nucleotide sequences and methods disclosed herein are useful in regulating expression of any heterologous nucleotide sequence in a host plant in order to vary the phenotype of a plant. Various changes in phenotype are of interest including modifying the fatty acid composition in a plant, altering the amino acid content of a plant, altering a plant's pathogen defense mechanism, altering the entry and exit of substances into the vascular tissue, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

In one embodiment of the present invention, the promoter sequences disclosed herein are operably linked to heterologous nucleotide sequences that modify the loading characteristics of vascular tissue and thereby affect plant development and maturation, carbon allocation, and crop yield. Phloem transports substances throughout the plant organism. Materials transported in the phloem include but are not limited to carbohydrates, amino acids, peptides, inorganic phosphate and invading pathogens. These substances transported by the phloem must be loaded or imported into the phloem, and numerous genes regulate phloem loading. By "vascular tissue loading" is intended loading and unloading of nutrients such as hormones, polypeptides, or carbohydrates into the cells of the plant vascular transport system. By altering the levels of substances involved in phloem loading, the loading characteristics of vascular tissue, plant development and plant growth can be influenced. The nucleotide sequences of the invention can be used to modulate expression of substances that regulate vascular tissue loading.

Substances that regulate vascular tissue loading include, but are not limited to, sucrose transporters encoded by SUT1 (Genbank Accession Nos. AF280050, AJ272309, AF167417, AF191025, AF191024, AF109922, X82275, AJ224961, X83850, X69165), SUT2 (Genbank Accession Nos.Y16768, AF166498, AJ272308) and SUT4 (Genbank Accession Nos. AF176950, AF175322, AF237780); sucrose synthases encoded by ASUS1 (Genbank Accession No. X70990), SUC1 (Genbank Accession No. X75365), SUC2 (Genbank Accession Nos. X75764, X79702), SUS1 (Genbank Accession No. L29418), Shrunken1 (Genbank Accession No. J01241), SS1 (Genbank Accession No. AJ001117) and SS2 (Marana et al. (1988) *Gene* 63:253–260); amino acid transporters encoded by NaAAP1 (Genbank Accession No. AF080542); peptide transporters encoded by NaAAP1 (Schultz, et al. (1999) *Plant J.* 6:637–646), galactinol synthases (Genbank Accession Nos. AF249912, AJ237693, AJ237694), inorganic pyrophosphatases (Genbank Accession No. AJ252210), K+ channel proteins encoded by AKT3 (Genbank Accession No. U44745), H+ ATPases encoded by AHA1 (Genbank Accession No. AJ002020), AHA2 (Harper et al. (1990) *J. Biol. Chem.* 265:13601–13608), AHA3 (DeWitt et al. (1991) *Plant J* 1:121–128), and pma4 (Gianinazzi-Pearson et al. (2000) *Planta* 211:609–613 and Genbank Accession No. X66737), amino acid permeases (Genbank Accession No. X71787), phloem carbohydrate regulators encoded by pgm (Genbank Accession No. AF216580) and sex1 (Genbank Accession No. AF312027), and fructosyltransferases genes (e.g Genbank Accession No. AJ250634). Each of these references, including those identified by their Genbank Accession Nos., is herein incorporated by reference.

In another embodiment of the invention, promoter sequences disclosed herein may be operably linked to heterologous nucleotide sequences useful in protecting plants against pathogens, said pathogens comprising insects, viruses, fungi, nematodes, and the like. Many pathogens travel through vascular tissue to spread disease through out the plant. Sap sucking insects transfer viruses, fungi and nematodes from infected plants to healthy plants. The invention allows vascular tissue-preferred, more specifically phloem tissue-preferred, expression of genes that confer antipathogenic activity. By "anti-pathogenic compositions" is intended that the compositions of the invention are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantify disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) *J. Biol. Chem.* 267:2228–2233, both of which are herein incorporated by reference).

Genes encoding disease resistance traits include, but are not limited to, detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

By "insect resistance" is intended that the plants avoid the symptoms and damage that are the outcome of plant-insect interactions. That is, insects are prevented from causing plant damage, crop damage, disfiguration of the plant, and plant disease, or alternatively, the plant damage, crop damage, disfiguration of the plant, and plant disease caused by the insect is minimized or lessened. Insect resistance genes of interest include toxin proteins from Bacillus, many of which are known in the art.

Heterologous nucleotide sequences of particular interest include sequences that impart an enhanced disease resistance to a variety of plant pests including insects with piercing and sucking mouth-parts that feed upon sap. For example, insects of the order Homoptera, often regarded as a separate suborder of the order Hemiptera, include those insects known as plant bugs. These pests include the aphids [family Aphididae], white flies [Aleyrodidae], planthoppers [Delphacidae], leafhoppers [Cicadellidae], jumping plant lice [Psyllidae] woolly aphids [Pemphigidae], mealy bugs [Pseudococcidae], and scales [Coccidae, Diaspididae, Asterolecaniidae, and Margarodidae]. Many species are serious pests of agricultural and horticultural crops and of ornamental plants, including, for example, pea aphid, black bean aphid; *Aphis gossypii*, cotton aphid; green apple aphid, glasshouse-potato aphid, leaf-curling plum aphid, banana aphid; *Brevicoryne brassicae*, cabbage aphid; turnip aphid, peach-potato aphid, corn leaf aphid, wheat aphid, brassica whitefly, tobacco whitefly, glasshouse whitefly, citrus blackfly, small brown planthopper, rice brown planthopper, sugarcane planthopper, white-backed planthopper, green rice leafhopper, beet leafhopper, cotton jassid, zig-zag winged rice leafhopper, apple sucker, pear sucker, woolly apple aphid, lettuce root woolly aphid, grape phylloxera, long-tailed mealybug, pineapple mealybug, striped mealybug, pink sugarcane mealybug, cottony cushion scale, olive scale, mussel scale, San Jose scale, California red scale, Florida red scale and coconut scale.

Also of interest are insect resistance genes that encode resistance to the plant-chewing stages of insects belonging to the orders Coleoptera, Lepidoptera and Orthoptera, including, but not limited to: *Acanthoscelides obtectus*; Bruchus sps.; Callosobruchus sps. [bruchid beetles]; Agriotes sps. [wireworms] particularly *Agrotis ipsilon*, black cutworm; Amphimallon sps. [chafer beetles]; *Anthonomus grandis* grandis, boll weevil; *Ceutorhynchus assimilis*, cabbage seed weevil; Cylas sps. [sweet potato weevils]; Diabrotica sps. [corn rootworms] particularly *Diabrotica virgifera*, western corn rootworm, *Diabrotica longicornis barberi*, northern corn rootworm, *Diabrotica undecimpunctata howardi*, southern corn rootworm; Epicauta sps. [black blister beetles]; Epilachna sps. [melon beetles etc.] particularly *Epilachna varivestis*, Mexican bean beetle; *Leptinotarsa decemlineata*, Colorado potato beetle; Meligisthes sps. [blossom beetles]; Melolontha sps. [cockchafers]; Phyleotreta sps.; Psylliodes sps. [flea beetles]; *Popillia japonica*, Japanese beetle; Scolytus sps. [bark beetles]; Sitophilus sps. [grain weevils] particularly *Sitophilus oryzae*, rice weevil; *Tenebrio molitor* [yellow mealworm]; Tribolium sps. [flour beetles]; *Trogoderma granarium*, Khapra beetle; Acleris sps. [fruit tree tortrixs]; *Acraea acerata*, sweet potato butterfly; Agrotis sps. [cutworms] particularly *Agrotis orthogonia*, western cutworm; *Autographa gamma*, silver-Y moth; Chilo sps. [stalk borers] particularly *Chilo partellus*, sorghum borer; *Cydia pomonella*, codling moth; Diparopsis sps. [red bollworms]; Ephestia sps. [warehouse moths]; Heliothis sps. particularly *Heliothis virescens*, cotton budworm; Helicoverpa sps. [budworms, bollworms] particularly Helicoverpa zea, cotton bollworm; *Mamestra brassicae*, cabbage moth; Manduca sps. [hornworms], *Maruca testulalis*, mung moth; Mythimna sps. [cereal armyworms]; *Ostrinia nubilalis*, European corn borer; *Pectinophora gossypiella*, pink bollworm; *Phthorimaea operculella*, potato tuber moth; *Pieris brassicae*, large white butterfly; *Pieris rapae*, small white butterfly; *Plodia interpunctella*, Indian grain moth; *Plutella xylostella*, diamond-back moth; *Sitatroga cerealella*, Angoumois grain moth; Spodoptera sps. [armyworms] particularly *Spodoptera frugiperda*, fall armyworm or corn earworm and *Spodoptera exigua*, beet armyworm; *Trichoplusia ni*, cabbage semilooper; Acheta sps. [field crickets]; Gryllotalph sps. [mole crickets]; *Locusta migratoria*, migratory locust; and *Schistocerca gregaria*, desert locust.

In addition, the promoter sequence of the invention allows vascular tissue-preferred expression of insect resistance genes that encode resistance to insect pests selected from the orders Diptera, Hymenoptera, Mallophaga, Thysanoptera, Dermaptera, Isoptera, Anoplura, Siphonaptera, Trichoptera, etc. Insect pests for the major crops include: Maize: *Diatraea grandiosella*, southwestern corn borer; *Elasmopalpus lignosellus*, lesser cornstalk borer; *Diatraea saccharalis*, surgarcane borer; Melanotus spp., wireworms; *Cyclocephala borealis*, northern masked chafer (white grub); *Cyclocephala immaculate*, southern masked chafer (white grub); *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Elasmopalpus lignosellus*, lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Elasmopalpus lignosellus*, lesser cornstalk borer; *Elasmopalpus lignosellus*, lesser cornstalk borer; *Oulema melanopus*, cereal leaf beetle; *Hypera punctata*, clover leaf weevil; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; Mayetiola destructor, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; zygogramma exciamationis, sunflower beetle; *Bothyrus gibbosus*, carrot beetle; *Neolasioptera murtfeldtiana*, sunflower seed midge; Cotton:; *Pseudatomoscelis seriatus*, cotton fleahopper; *Trialeurodes abutilonea*, banded winged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Colaspis brunnea*, grape colaspis; *Lissorhoptrus oryzophilus*, rice water weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Phyllotreta cruciferae*, Flea beetle; *Mamestra configurata*, Bertha armyworm; Delia ssp., Root maggots.

Nucleotide sequences that encode polypeptides that impart an enhanced insect resistance are known in the art. For example, such sequences include, but are not limited to, sequences encoding *Bacillus thuringiensis* toxic proteins (U.S. Pat. Nos. 5,366,892; 5,747,450; 5,736,514; 5,723,756; 5,593,881; 6,110,464; 6,033,874; 6,015,891; 5,942,664; 5,914,318; 5,567,600; 5,567,862; 5,723,440; 6,153,814; 6,063,756; 5,854,053; 5,854,053; Geiser et al. (1986) *Gene* 48:109); lectins, wherein the lectin comprises snowdrop lectin, pea lectin, jackbean lectin, modified jack bean lectin, wheatgerm lectin, potato lectin, peanut lectin or wheatgerm agglutinin, aprotinin, and *Hernandia moerenhoutiana* lectin (Zhou et al. (1998) *Chin J. Biotechnol* 14:9; Van Damme et al. (1994) *Plant Mol. Biol.* 24:825; U.S. Pat. No. 5,545,820; WO 9416565A1; and WO 00/44780); lipoxidases, wherein the lipoxidase comprises pea lipoxidase 1 or soybean lipoxidase; insect chitinases (U.S. Pat. No. 5,866,788); insecticidal polypeptides (U.S. Pat. No. 5,824,864); and the like. All of these references are herein incorporated by reference.

Sap sucking pests transfer viruses from infected plants to healthy plants. Such viruses include rice tungro bacilliform virus (Bhattacharyya-Pakrasi et al. (1993) *Plant J.* 4:71), tobacco mosaic virus (Cheng et al.(2000) *Plant J.* 3:349), sweet potato chlorotic stunt virus, and sweet potato feather mottle virus (Karyeija et al. (2000) *Virology* 269:26). Phloem-preferred expression of a heterologous nucleotide sequence with antipathogenic activity lessens or minimizes the impact of the viral pathogens.

Additional pathogens of interest include, but are not limited to, viruses or viroids and fungi. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata,* Soybean mosaic virus, *Glomerella glycines,* Tobacco Ring spot virus, Tobacco Streak virus, *Phakopsora pachyrhizi, Pythium aphanidermatum, Pythium ultimum, Pythium debaryanum,* Tomato spotted wilt virus, *Heterodera glycines Fusarium solani;* Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata;* Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae;* Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium graminearum, Collotetrichum graminicola, Erysiphe graminis* f.sp. *tritici, Puccinia graminis* f.sp. *tritici, Puccinia recondite* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum,* High Plains Virus, European wheat striate virus; Sunflower: *Plasmophora halstedii, Sclerotinia sclerotiorum,* Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis;* Corn: *Fusarium moniliforme* var. *subglutinans, Erwinia stewartii, Fusarium moniliforme, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride,* Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora,* Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi,* Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

Nematodes include parasitic nematodes such as root-knot, cyst, and lesion nematodes, including Heterodera and Globodera spp; particularly *Globodera rostochiensis* and *Globodera pailida* (potato cyst nematodes); *Heterodera glycines* (soybean cyst nematode); *Heterodera schachtii* (beet cyst nematode); and *Heterodera avenae* (cereal cyst nematode).

A further embodiment of the invention allows expression of herbicide resistance traits. Herbicide resistance traits may be introduced into plants by genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations). Also of interest are genes coding for resistance to herbicides that act to inhibit action of glutamine synthase, such as phosphinothricin or basta (e.g., the bar gene), or other such genes known in the art. The bar gene encodes resistance to the herbicide basta, and the ALS-gene mutants encode resistance to the herbicide chlorsulfuron.

It is further recognized that the nucleotide sequences of interest used in the present invention are reflective of the commercial markets and the interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly.

General categories of nucleotide sequences of interest include for example, those genes involved in information, such as zinc fingers, those involved in communication, such as kinases, those involved in housekeeping, such as heat shock proteins, and those involved in phloem loading, such as transporters. More specific categories of transgenes, for example, include genes encoding important traits for agronomics, insect resistance, disease resistance, herbicide resistance, exudate characteristics, and commercial products. Nucleotide sequences of interest further include, generally, those involved in oil, starch, carbohydrate, or nutrient metabolism as well as those affecting kernel size, sucrose loading, nutrient transport and the like.

Agronomically important traits such as oil, starch, and protein content can be genetically altered using the methods of the present invention. Modifications include increasing content of oleic acid, saturated and unsaturated oils, increasing levels of lysine and sulfur, providing essential amino acids, and modifying starch. Hordothionin protein modifications are described in U.S. patent application Ser. No. 08/838,763, filed Apr. 10, 1997; Ser. No. 08/824,379, filed Mar. 26, 1997; Ser. No. 08/824,382, filed Mar. 26, 1997; and U.S. Pat. No. 5,703,049; herein incorporated by reference. Another example is lysine and/or sulfur rich seed protein encoded by the soybean 2S albumin described in U.S. Ser. No. 08/618,911, filed Mar. 20, 1996, and the chymotrypsin inhibitor from barley, Williamson et al. (1987) *Eur. J. Biochem.* 165:99–106, the disclosures of which are herein incorporated by reference.

Derivatives of the coding sequences can be made by site directed mutagenesis to increase the level of preselected amino acids in the encoded polypeptide. For example, the gene encoding the barley high lysine polypeptide (BHL) is derived from barley chymotrypsin inhibitor, U.S. Ser. No. 08/740,682, filed Nov. 1, 1996, and PCT/US97/20441, filed Oct. 31, 1997, the disclosures of each are incorporated herein by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference)); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

The quality of grain is reflected in traits such as levels and types of oils, saturated and unsaturated, quality and quantity of essential amino acids, and levels of cellulose. In corn, modified hordothionin proteins, described in U.S. patent application Ser. No. 08/838,763, filed Apr. 10, 1997; Ser. No. 08/824,379, filed Mar. 26, 1997; Ser. No. 08/824,382, filed Mar. 26, 1997; and U.S. Pat. No. 5,703,049 issued Dec. 30, 1997, provide descriptions of modifications of proteins for desired purposes.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321 issued Feb. 11, 1997. Genes such as B-Ketothiolase, PHBase (polyhydroxyburyrate synthase) and acetoacetyl-CoA reductase (see Schubert et al. (1988) *J. Bacteriol.* 170:5837–5847) facilitate expression of polyhyroxyalkanoates (PHAs). A particular embodiment of the invention encompasses phloem-preferred expression of said polymers and bioplastics to facilitate collection and harvest of these products from the exudate or plant sap.

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The expression cassette comprising the promoter sequence of the present invention operably linked to a nucleotide sequence of interest can be used to transform any plant species, including, but not limited to, monocotyledons and dicotyledons. Examples of plant species of interest include, but are not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta* vulgaris), sugarcane (Saccharum spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus Cucumis such as cucumber (*C. sativus*), cantaloupe (*C. cantalupensis*), and muskmelon (*C. melo*). Ornamentals include azalea (Rhododendron spp.), hydrangea (*Macrophylla hydrangea*), hibiscus (*Hibiscus rosasanensis*), roses (Rosa spp.), tulips (Tulipa spp.), daffodils (Narcissus spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:43054309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin. et al. (1992) *Plant Cell* 4:1495–1505 (electroporation); Li et al. (1993) *Plant Cell Reports* 12:250-255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The following examples are offered by way of illustration and not by way of limitation.

Experiments

EXAMPLE 1

Isolation of Promoter Sequences

The promoter region for the *Prunus serotina* gene encoding prunasin hydrolase was isolated from cherry trees utilizing the GenomeWalker Kit™ (Clontech). The sequence for the prunasin hydrolase promoter is set forth in SEQ ID NO.: 1. The sequence for the prunasin hydrolase operon including the prunasin hydrolase promoter region is set forth in SEQ ID NO.: 3. Nucleotides 989–2626 of SEQ ID NO.: 3 encode a prunasin hydrolase polypeptide.

Genomic DNA was extracted from Black Cherry (*Prunus serotina*) leaves using the "DNeasy Plant mini kit" (Qiagen Cat# 69104). The protocol was followed as written (November 1999 edition). Five GenomeWalker™ libraries were then created from that Genomic DNA according to the manual for the "Universal GenomeWalker™ Kit" (Clontech K1807-1). They were created using blunt cutting enzymes:

| Library | Enzyme |
|---|---|
| DL-1 | EcoRV |
| DL-2 | ScaI |
| DL-3 | DraI |
| DL-4 | PvuII |
| DL-5 | StuI |

Gene specific primers (GSP1/SEQ ID NO.: 7 and GSP2/SEQ ID NO.:8) were designed using known sequence for prunasin hydrolase (Genbank Acc. No. U50201).

Prunasin Hydrolase GenomeWalker ™ Primers

GSP1/ 5'-GTATCGAAATGGGTCCTGTTGAGAGT SEQ ID NO.:7

GSP2/ 5'-ATATGTCCCGGCAGCATTGGTATTTG SEQ ID NO.:8

Amplifications were then carried out according to the manual for the "Universal GenomeWalker™ Kit", using the GSP1 primer for the primary GenomeWalker™ amplification and GSP2 for the secondary amplification. A 1.5 kb band was produced in the DL-1 library. This fragment was cloned into pGEMT-easy (Promega Cat#A1360) and sequenced. Results from the sequence indicated that two different products were present in the cloned product. They were designated DL1.4 and DL1.1. Both products were confirmed to be genomically adjacent to the prunasin hydrolase by amplifying products using forward primers based on sequence from the GenomeWalker™ fragments and reverse primers from the prunasin hydrolase sequence. Once confirmed, the PH DL1.1 and PH DL1.4 promoters were then amplified from the Black Cherry Genomic DNA using the primers below to add NcoI sites at the start codon. The fragments produced were cloned into pGEMT-easy and sequenced for confirmation.

Prunasin Hydrolase Promoter PCR Primers

DL1.1/SEQ ID NO.: 5

Product of length 1260(rating: 162
puts NcoI at start codon)
Tm: 74.5 C TaOpt: 54.0 C GC: 36.8

| ACCGTGCGAAAGGTCTTCTTG | SEQ ID NO.:9 |
| ATGCCATGGCTGAGAGGAGGG | SEQ ID NO.:10 |

DL1.4/SEQ ID NO.: 1

Product of length 871 (rating: 162)
(puts NcoI at start codon)
Tm: 73.7 C TaOpt: 55.6 C GC: 35.6

| GGGGTGCTTACACCCACAATCATCC | SEQ ID NO.:11 |
| GCAATGCCATGGCTCAGTGGAG | SEQ ID NO.:12 |

EXAMPLE 2

Transformation and Regeneration of Transgenic Plants

Immature maize embryos from greenhouse donor plants are bombarded with a plasmid containing the prunasin hydrolase promoter operably linked to a heterologous nucleotide sequence and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% bleach plus 0.5% detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the prunasin hydrolase promoter operably linked to a heterologous nucleotide sequence is made. This vector plus a PAT selectable marker, either in the same or a separate vector, are precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for expression of the heterologous nucleotide sequence.

Bombardment and Culture Media

Bombardment medium (560Y) comprises 4.0 g/l N6 basal salts (SIGMA C-1416), 1.0 ml/l Eriksson's Vitamin Mix (1000X SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000X SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117–074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 µl myo-inositol, and 40.0 g/l sucrose (brought to volume with polished D-I $H_2O$ after adjusting pH to 5.6); and 6 g/l bacto-agar (added after bringing to volume with polished D-l $H_2O$), sterilized and cooled to 60° C.

EXAMPLE 3
Agrobacterium-Mediated Transformation of Maize

For Agrobacterium-mediated transformation of maize with a prunasin hydrolase promoter of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the prunasin hydrolase promoter operably linked to a heterologous nucleotide sequence of interest to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Gus Fusion Construct Transformation in Maize

A construct containing the prunasin hydrolase promoter fused to GUS was used to transform maize the method of Zhao supra. A total of 3 plants per event were generated and transplanted in the greenhouse.

GUS Detection Protocol

Various tissue samples collected from transgenic plants were hand sectioned, and GUS expression patterns checked histochemically by staining overnight in a staining solution at 37° C. The solution contained 0.1 M phosphate buffer, pH 7.5, 0.1% Triton X-100 and 0.5 mg/mL 5-bromo-4-chloro-3-indolyl-β-D-glucuronide (X-gluc). The GUS enzyme produced in cells expressing the transgenes would convert X-gluc to a blue precipitate in situ, thus allowing localization of the transgenes (Jefferson et al., 1987 EMBO J 6:3901). Chlorophyll from green tissues was bleached with 75% ethanol to facilitate the visualization of the blue staining from GUS expression. Tissue sections were then examined and photographed under a dissecting microscope.

GUS Expression in Maize

Leaf midrib samples from 16 events were surveyed for GUS expression. Fifteen of the 16 events contained detectable staining using the histochemical assay. Plants for 10 events were chosen randomly for additional surveys, with samples from 5 of these events taken from multiple time points to detect expression in developing kernels. A variety of tissues and organs were surveyed, and GUS expression was consistently found in the vascular bundles. In some tissue sections, diffusion into surrounding cells near vascular bundles was also observed. The expression data collected on these plants indicate that the prunasin promoter was fully active in maize, and that it's specificity for vascular tissue was preserved. FIGS. 3 and 4 further detail the vascular tissue expression associated with maize transformation with the GUS/prunasin promoter construct.

EXAMPLE 4
Soybean Embryo Transformation

Soybean embryos are bombarded with a plasmid containing the prunasin hydrolase promoter operably linked to a heterologous nucleotide sequence of interest (FIG. 1) as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the prunasin hydrolase promoter operably linked to the heterologous nucleotide sequence can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 5

Sunflower Meristem Tissue Transformation

Sunflower meristem tissues are transformed with an expression cassette containing the prunasin hydrolase promoter operably linked to a heterologous nucleotide sequence as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep.* 9:55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.* 15:473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar.

The explants are subjected to microprojectile bombardment prior to Agrobacterium treatment (Bidney et al. (1992) *Plant Mol. Biol.* 18:301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the prunasin hydrolase promoter operably linked to the heterologous nucleotide sequence is introduced into Agrobacterium strain EHA105 via freeze-thawing as described by Holsters et al. (1978) *Mol. Gen. Genet.* 163:181–187. This plasmid further comprises a kanamycin selectable marker gene (i.e, nptll). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The Agrobacterium cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an Agrobacterium suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for prunasin hydrolase promoter driven expression of the heterologous nucleotide sequence.

NPTII-positive shoots are grafted to Pioneer® (hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by transcription activity analysis of leaf extracts while transgenic seeds harvested from NPTII-positive To plants are identified by transcription activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8

μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l NH$_4$Cl and 0.3 g/l MgSO$_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for expression using assays known in the art such as Northern blot. After positive (i.e., for prunasin hydrolase promoter driven expression) explants are identified, those shoots that fail to exhibit prunasin hydrolase promoter driven expression are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for prunasin hydrolase promoter regulated expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

EXAMPLE 6

GUS Fusion Construct Transformation into Arabidopsis

A construct containing the prunasin hydrolase promoter fused to GUS was used to transform Arabidopsis by method of Bechtold and Pelletier. (N. Bechtold and G. Pelletier *In Planta Agrobacterium-mediated transformation of adult Arabidopsis thaliana plants by vacuum infiltration, in ARABIDOPSIS PROTOCOLS*. METHODS IN MOLECULAR BIOLOGY Vol. 82, pp 259–266 (J. M. Martinez-Zapater and J. Salinas, eds., Humana Press, Totowa, N.J.).

Arabidopsis Transformation

4–6 week old Arabidopsis plants were removed from the soil carefully, to keep root systems intact. The roots were then rinsed with water to remove any soil particles attached to them. 25–50 plants were placed in an aluminum tray. A second perforated tray of the same size was positioned on top of the first tray to prevent movement of the plants. An Agrobacterium suspension was then poured into the trays. The trays were then placed in a 10-L vacuum chamber. A vacuum pressure of $10^4$ Pa (0.1 atm) was applied for 20 minutes. During the vacuum processing, a plastic tray filled with compost, treat and water was prepared. The vacuum was broken gently, and the trays removed from the chamber. The infiltrated plants were replanted immediately and covered with a perforated plastic wrap or seed tray incubator with water underneath. The covering was removed from the plants after 3–4 days. The plants were allowed to continue growing, with moderate watering, until the desired maturity was reached.

GUS Detection Protocol

Various tissue samples collected from transgenic plants were hand sectioned, and GUS expression patterns checked histochemically by staining overnight in a staining solution at 37° C. The solution contained 0.1 M phosphate buffer, pH 7.5, 0.1% Triton X-100 and 0.5 mg/mL 5-bromo-4-chloro-3-indolyl-β-D-glucuronide (X-gluc). The GUS enzyme produced in cells expressing the transgenes would convert X-gluc to a blue precipitate in situ, thus allowing localization of the transgenes (Jefferson et al., 1987 EMBO J 6:3901). Chlorophyll from green tissues was bleached with 75% ethanol to facilitate the visualization of the blue staining from GUS expression. Tissue sections were then examined and photographed under a dissecting microscope.

Figure 5:
FIG. 5 demonstrates GUS expression in Arabidopsis plants following in planta Agrobacterium-mediated transformation.

FIG. 5 further details the vascular tissue expression associated with Arabidopsis transformation utilizing the GUS/prunasin promoter construct.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

What is claimed is:

1. An isolated promoter comprising the nucleotide sequence set forth in SEQ ID NO: 1 or SEQ ID NO: 2.

2. An expression cassette comprising the isolated promoter of claim 1 operably linked to a heterologous nucleotide sequence of interest.

3. An expression vector comprising the expression cassette of claim 2.

4. A host cell having stably incorporated into its genome the expression cassette of claim 2.

5. A plant cell having stably incorporated into its genome the expression cassette of claim 2.

6. The plant cell of claim 5, wherein said plant cell is from a dicotyledonous plant.

7. The plant cell of claim 5, wherein said plant cell is from a monocotyledonous plant.

8. A transformed plant having stably incorporated into its genome an isolated promoter comprising the nucleotide sequence set forth in SEQ ID NO: 1 or SEQ ID NO: 2.

9. The plant of claim 8, wherein said plant is a dicotyledonous plant.

10. The plant of claim 8, wherein said plant is a monocotyledonous plant.

11. A seed of the plant of claim 8, wherein the seed comprises the isolated promoter.

12. A method for expressing a heterologous nucleotide sequence in a plant, said method comprising stably integrating into a plant a heterologous nucleotide sequence of interest operably linked to a promoter, wherein the promoter comprises the nucleotide sequence set forth in SEQ ID NO: 1 or SEQ ID NO: 2.

13. The method of claim 12, wherein said plant is dicotyledonous.

14. The method of claim 12, wherein said plant is monocotyledonous.

15. The method of claim 12, wherein said heterologous nucleotide sequence of interest is preferentially expressed in vascular tissue.

16. The method of claim 15, wherein said vascular tissue is phloem tissue.

17. The method of claim 12, wherein the heterologous nucleotide sequence of interest encodes a polypeptide having antipathogenic activity.

18. The method of claim 17, wherein the heterologous nucleotide sequence encodes a polypeptide having antipathogenic activity towards insects.

19. The method of claim 12, wherein said heterologous nucleotide sequence of interest encodes a polypeptide that regulates vascular tissue loading.

* * * * *

SEQUENCE LISTING

<160> NUMBER OF SEQ ID NOS: 13

<210> SEQ ID NO 1
<211> LENGTH: 988
<212> TYPE: DNA
<213> ORGANISM: Prunus serotina

<400> SEQUENCE: 1

| | | | | | |
|---|---|---|---|---|---|
| accttaaagg | acgtccctca | aataaaatta | tttgagagat | tcctcaatag | aagggatta | 60 |
| tatatatata | tatatacatt | ccaggtagaa | ggtgctgcaa | acgaaggtgg | taggggacca | 120 |
| agcatatggg | gtgcttacac | ccacaatcat | ccaggtctac | ttattttctc | caaatccttt | 180 |
| tatggtttca | actagtcagt | gcccttttgct | ctcacaatta | agtccacata | tgtggactac | 240 |
| agtaattaaa | catatggttt | tcaatgtcta | aacaagccaa | tacttcatgg | atttgagtta | 300 |
| tgcatggcat | accgttctgt | tttaagtgtt | attaaagtgc | ctgcaaggaa | ttcttacaag | 360 |
| gatacaattc | tatactaata | ccaatacaag | ataacataac | aaaatactaa | ttcgctctga | 420 |
| catcaatggc | acacaatgag | gtgacaagtt | tccgagaaag | ttagagaaaa | tgttacttgc | 480 |
| attctccaat | ttaatatcta | aatagctaaa | ttactttgtg | cttttaatta | ctaatagtca | 540 |
| tgtaatatgt | atatttggtc | tacagacata | cacgcacaca | ctagtttaca | tgatctgatt | 600 |
| tcccaaactt | tatgcttaaa | taaaaataat | ctttggttaa | ttgcgagaga | aatttgtttt | 660 |
| gagcaattaa | tgccaattga | tggagatagg | agagaaaaca | ttaatggaga | agggtgcaat | 720 |
| tagattatct | ttccaaaacc | agaggttagg | gcacgggagc | aaaaccagac | tctgaaggtg | 780 |
| atcccaatgg | aatctttgga | ttgcttttcc | atactttagc | tttaaagccc | ctgcttggct | 840 |
| ttacaaaaaa | gaaagcaaaa | aagaaagcaa | aatgctttttg | atttattatt | tcacgtgta | 900 |
| gaagttatgt | actccttcta | tataaatccc | atgcaatata | gcaggaagag | cacacctagc | 960 |
| tcgatcataa | aaaatcctcc | actgagtt | | | | 988 |

<210> SEQ ID NO 2
<211> LENGTH: 865
<212> TYPE: DNA
<213> ORGANISM: Prunus serotina

<400> SEQUENCE: 2

| | | | | | |
|---|---|---|---|---|---|
| tggggtgctt | acacccacaa | tcatccaggt | ctacttattt | tctccaaatc | cttttatggt | 60 |
| ttcaactagt | cagtgccctt | tgctctcaca | attaagtcca | catatgtgga | ctacagtaat | 120 |
| taaacatatg | gttttcaatg | tctaaacaag | ccaatacttc | atggatttga | gttatgcatg | 180 |
| gcataccgtt | ctgttttaag | tgttattaaa | gtgcctgcaa | ggaattctta | caaggataca | 240 |
| attctatact | aataccaata | caagataaca | taacaaaata | ctaattcgct | ctgacatcaa | 300 |
| tggcacacaa | tgaggtgaca | agtttccgag | aaagttagag | aaaatgttac | ttgcattctc | 360 |
| caatttaata | tctaaatagc | taaattactt | tgtgctttta | attactaata | gtcatgtaat | 420 |
| atgtatattt | ggtctacaga | catacacgca | cacactagtt | tacatgatct | gatttcccaa | 480 |
| actttatgct | taaataaaaa | taatctttgg | ttaattgcga | gagaaatttg | ttttgagcaa | 540 |
| ttaatgccaa | ttgatggaga | taggagagaa | acattaatg | gagaagggtg | caattagatt | 600 |
| atctttccaa | aaccagaggt | tagggcacgg | gagcaaaacc | agactctgaa | ggtgatccca | 660 |
| atggaatctt | tggattgctt | ttccatactt | tagctttaaa | gccccctgctt | ggctttacaa | 720 |
| aaaagaaagc | aaaaaagaaa | gcaaaatgct | tttgatttat | tattttcacg | tgtagaagtt | 780 |

-continued

| | |
|---|---|
| atgtactcct tctatataaa tcccatgcaa tatagcagga agagcacacc tagctcgatc | 840 |
| ataaaaaatc ctccactgag ccatg | 865 |

<210> SEQ ID NO 3
<211> LENGTH: 2998
<212> TYPE: DNA
<213> ORGANISM: Prunus serotina
<220> FEATURE:
<221> NAME/KEY: CDS
<222> LOCATION: (989)...(2626)

<400> SEQUENCE: 3

| | |
|---|---|
| accttaaagg acgtccctca aataaaatta tttgagagat tcctcaatag aagggaatta | 60 |
| tatatatata tatatacatt ccaggtagaa ggtgctgcaa acgaaggtgg taggggacca | 120 |
| agcatatggg gtgcttacac ccacaatcat ccaggtctac ttattttctc caaatccttt | 180 |
| tatggtttca actagtcagt gcccttttgct ctcacaatta agtccacata tgtggactac | 240 |
| agtaattaaa catatggttt tcaatgtcta aacaagccaa tacttcatgg atttgagtta | 300 |
| tgcatggcat accgttctgt tttaagtgtt attaaagtgc ctgcaaggaa ttcttacaag | 360 |
| gatacaattc tatactaata ccaatacaag ataacataac aaaatactaa ttcgctctga | 420 |
| catcaatggc acacaatgag gtgacaagtt tccgagaaag ttagagaaaa tgttacttgc | 480 |
| attctccaat ttaatatcta aatagctaaa ttactttgtg cttttaatta ctaatagtca | 540 |
| tgtaatatgt atatttggtc tacagacata cacgcacaca ctagtttaca tgatctgatt | 600 |
| tcccaaactt tatgcttaaa taaaaataat ctttggttaa ttgcgagaga aatttgtttt | 660 |
| gagcaattaa tgccaattga tggagatagg agagaaaaca ttaatggaga agggtgcaat | 720 |
| tagattatct ttccaaaacc agaggttagg gcacgggagc aaaaccagac tctgaaggtg | 780 |
| atcccaatgg aatctttgga ttgcttttcc atactttagc tttaaagccc ctgcttggct | 840 |
| ttacaaaaaa gaaagcaaaa aagaaagcaa aatgcttttg atttattatt ttcacgtgta | 900 |
| gaagttatgt actccttcta tataaatccc atgcaatata gcaggaagag cacacctagc | 960 |
| tcgatcataa aaaatcctcc actgagtt atg gca ttg caa ttc cgc tct ttg | 1012 |
|                                                   Met Ala Leu Gln Phe Arg Ser Leu | |
|                                               1             5 | |
| ctc ttg tgt gtg gtg ctg ctt ctc ctt ggc ttt gca ttg gca aat acc | 1060 |
| Leu Leu Cys Val Val Leu Leu Leu Leu Gly Phe Ala Leu Ala Asn Thr | |
|  10                 15                    20 | |
| aat gct gcc ggg aca tat cca ccc gtt gtt tgt gca act ctc aac agg | 1108 |
| Asn Ala Ala Gly Thr Tyr Pro Pro Val Val Cys Ala Thr Leu Asn Arg | |
| 25                  30                   35                  40 | |
| acc cat ttc gat act ctt ttt cca ggg ttc aca ttt ggc gca gct aca | 1156 |
| Thr His Phe Asp Thr Leu Phe Pro Gly Phe Thr Phe Gly Ala Ala Thr | |
|                45                   50                   55 | |
| gcg gct tac caa tta gaa ggt gct gca aac ata gat ggt aga gga cca | 1204 |
| Ala Ala Tyr Gln Leu Glu Gly Ala Ala Asn Ile Asp Gly Arg Gly Pro | |
|           60                  65                   70 | |
| agc gta tgg gat aac ttc acc cac gaa cat cca gaa aag ata act gat | 1252 |
| Ser Val Trp Asp Asn Phe Thr His Glu His Pro Glu Lys Ile Thr Asp | |
|         75                  80                   85 | |
| ggc agc aat gga gat gtt gct att gat caa tat cac cgt tat aag gaa | 1300 |
| Gly Ser Asn Gly Asp Val Ala Ile Asp Gln Tyr His Arg Tyr Lys Glu | |
|      90                  95                100 | |
| gat gtg gca att atg aag gat atg ggg ttg gat gct tat agg ttc tct | 1348 |
| Asp Val Ala Ile Met Lys Asp Met Gly Leu Asp Ala Tyr Arg Phe Ser | |
| 105                110                115              120 | |

```
atc tca tgg tcc aga tta tta cca aat ggg aca cta agt ggt gga att      1396
Ile Ser Trp Ser Arg Leu Leu Pro Asn Gly Thr Leu Ser Gly Gly Ile
            125                 130                 135 aac aag aag gga atc gaa tac tac aat aat ctg acc aat gaa ctc cta      1444
Asn Lys Lys Gly Ile Glu Tyr Tyr Asn Asn Leu Thr Asn Glu Leu Leu
        140                 145                 150 cgc aat ggt ata gag cca tta gtg aca ctc ttc cac tgg gat gtt ccc      1492
Arg Asn Gly Ile Glu Pro Leu Val Thr Leu Phe His Trp Asp Val Pro
            155                 160                 165 caa gcc tta gta gac gaa tat gat ggt ttg tta agc cct cgt att gtc      1540
Gln Ala Leu Val Asp Glu Tyr Asp Gly Leu Leu Ser Pro Arg Ile Val
170                 175                 180 gat gac ttt gaa gca tac gca aac ctt tgt tat aag gaa ttt ggt gat      1588
Asp Asp Phe Glu Ala Tyr Ala Asn Leu Cys Tyr Lys Glu Phe Gly Asp
185                 190                 195                 200 cga gta aag cat tgg acc aca ctt aat gag cca tat acc gtt agt aac      1636
Arg Val Lys His Trp Thr Thr Leu Asn Glu Pro Tyr Thr Val Ser Asn
            205                 210                 215 cat ggt tac aca atc ggg atc cac gca cca gga cga tgc tct tgt tgg      1684
His Gly Tyr Thr Ile Gly Ile His Ala Pro Gly Arg Cys Ser Cys Trp
            220                 225                 230 tat gac cca acc tgc ctt ggt gga gat tcg ggt act gaa cca tat ctc      1732
Tyr Asp Pro Thr Cys Leu Gly Gly Asp Ser Gly Thr Glu Pro Tyr Leu
            235                 240                 245 gtg aca cac cac cta ctc ctt gct cat gct gct gct gta aaa ctg tac      1780
Val Thr His His Leu Leu Leu Ala His Ala Ala Ala Val Lys Leu Tyr
        250                 255                 260 agg gaa aaa tat cag gca agt caa aat ggt gtg ata gga ata aca att      1828
Arg Glu Lys Tyr Gln Ala Ser Gln Asn Gly Val Ile Gly Ile Thr Ile
265                 270                 275                 280 gta tca cat tgg ttt gag ccg gct tcg gag tca caa caa gat aaa gac      1876
Val Ser His Trp Phe Glu Pro Ala Ser Glu Ser Gln Gln Asp Lys Asp
            285                 290                 295 gct gca tct cga gct ttg gat ttt atg tat gga tgg ttt atg gag cca      1924
Ala Ala Ser Arg Ala Leu Asp Phe Met Tyr Gly Trp Phe Met Glu Pro
            300                 305                 310 ttg aca aga gga gac tac ccg cag acc atg cga tct att gtt ggc tca      1972
Leu Thr Arg Gly Asp Tyr Pro Gln Thr Met Arg Ser Ile Val Gly Ser
            315                 320                 325 cga tta cct aat ttc aca gaa gaa caa tcc aag tca ctg aat ggg tca      2020
Arg Leu Pro Asn Phe Thr Glu Glu Gln Ser Lys Ser Leu Asn Gly Ser
        330                 335                 340 tat gac tac att gga gta aac tac tat tct gcc aga tat gca agc gct      2068
Tyr Asp Tyr Ile Gly Val Asn Tyr Tyr Ser Ala Arg Tyr Ala Ser Ala
345                 350                 355                 360 tat act aat aat tat tct gta cct aca cct cca agc tac gca aca gat      2116
Tyr Thr Asn Asn Tyr Ser Val Pro Thr Pro Pro Ser Tyr Ala Thr Asp
            365                 370                 375 gct tat gtt aat gtc aca aca act gat ctt aat gga gtc cct att ggt      2164
Ala Tyr Val Asn Val Thr Thr Thr Asp Leu Asn Gly Val Pro Ile Gly
            380                 385                 390 cca cag gct gct tcg gac tgg tta tat gtt tac cca aaa gga ctt tac      2212
Pro Gln Ala Ala Ser Asp Trp Leu Tyr Val Tyr Pro Lys Gly Leu Tyr
            395                 400                 405 gat ctt gta ctc tac aca aaa gaa aag tat aat gat cca gtt atg tac      2260
Asp Leu Val Leu Tyr Thr Lys Glu Lys Tyr Asn Asp Pro Val Met Tyr
            410                 415                 420 att act gag aat ggt atg gat gag ttc aat aat ccc aaa tta tca ctt      2308
Ile Thr Glu Asn Gly Met Asp Glu Phe Asn Asn Pro Lys Leu Ser Leu
```

-continued

```
                  425                 430                 435                 440
gag gaa gcc ctt gat gat gct aat aga att gac tac tac tat cgc cac                    2356
Glu Glu Ala Leu Asp Asp Ala Asn Arg Ile Asp Tyr Tyr Tyr Arg His
                          445                 450                 455 ctc tgt tac ctc caa gca gca att aag gag ggt gct aat gtg cag gga                    2404
Leu Cys Tyr Leu Gln Ala Ala Ile Lys Glu Gly Ala Asn Val Gln Gly
                460                 465                 470 tac ttc gca tgg tca ttg tta gac aac ttt gaa tgg agc gaa gga tac                    2452
Tyr Phe Ala Trp Ser Leu Leu Asp Asn Phe Glu Trp Ser Glu Gly Tyr
        475                 480                 485 acg gtt cgg ttt ggt atc aac tat att gat tac gac aat gga ttg gaa                    2500
Thr Val Arg Phe Gly Ile Asn Tyr Ile Asp Tyr Asp Asn Gly Leu Glu
490                 495                 500 aga cac tca aaa ctc tca acg cac tgg ttc aaa agt ttc ctc aag aga                    2548
Arg His Ser Lys Leu Ser Thr His Trp Phe Lys Ser Phe Leu Lys Arg
505                 510                 515                 520 tcc tca att agt aag aaa aaa atc cga aga tgt ggt aac aat aat gct                    2596
Ser Ser Ile Ser Lys Lys Lys Ile Arg Arg Cys Gly Asn Asn Asn Ala
                525                 530                 535 aag gct acc aaa ttt gtg tat caa atg tga atcccaatga tggataaagt                      2646
Lys Ala Thr Lys Phe Val Tyr Gln Met *
                540                 545 acagtggctg ctccatagtc gtcatgtgag ttgtgtttat gttttractt tttgtttggc                   2706
tctttctgag tcggaataag ttgcaacaac tcattatgag ttagttgtct atcgttgtga                   2766
gagtttaatt ttaattttgc tttatgtttt tgatgtgccc cgtttatcca agtttgttgg                   2826
ctttatgccg tgttggtgct ttggccattt gtggatatgg ttggaaggat atacctaatt                   2886
gtctagatgt tgatatatcc ctcatgtgtt tgtcttagtc cttgtggtca gtagcccttt                   2946
atggctaaat tatgaatgaa atttcctcta ataaaaact agaataaaaa aa                            2998
```

<210> SEQ ID NO 4
<211> LENGTH: 545
<212> TYPE: PRT
<213> ORGANISM: Prunus serotina

<400> SEQUENCE: 4

```
Met Ala Leu Gln Phe Arg Ser Leu Leu Cys Val Val Leu Leu Leu
1               5                   10                  15

Leu Gly Phe Ala Leu Ala Asn Thr Asn Ala Ala Gly Thr Tyr Pro Pro
                20                  25                  30

Val Val Cys Ala Thr Leu Asn Arg Thr His Phe Asp Thr Leu Phe Pro
            35                  40                  45

Gly Phe Thr Phe Gly Ala Ala Thr Ala Ala Tyr Gln Leu Glu Gly Ala
        50                  55                  60

Ala Asn Ile Asp Gly Arg Gly Pro Ser Val Trp Asp Asn Phe Thr His
65                  70                  75                  80

Glu His Pro Glu Lys Ile Thr Asp Gly Ser Asn Gly Asp Val Ala Ile
                85                  90                  95

Asp Gln Tyr His Arg Tyr Lys Glu Asp Val Ala Ile Met Lys Asp Met
                100                 105                 110

Gly Leu Asp Ala Tyr Arg Phe Ser Ile Ser Trp Ser Arg Leu Leu Pro
            115                 120                 125

Asn Gly Thr Leu Ser Gly Gly Ile Asn Lys Lys Gly Ile Glu Tyr Tyr
        130                 135                 140

Asn Asn Leu Thr Asn Glu Leu Leu Arg Asn Gly Ile Glu Pro Leu Val
145                 150                 155                 160
```

-continued

```
Thr Leu Phe His Trp Asp Val Pro Gln Ala Leu Val Asp Glu Tyr Asp
            165                 170                 175
Gly Leu Leu Ser Pro Arg Ile Val Asp Phe Glu Ala Tyr Ala Asn
        180                 185                 190
Leu Cys Tyr Lys Glu Phe Gly Asp Arg Val Lys His Trp Thr Thr Leu
        195                 200                 205
Asn Glu Pro Tyr Thr Val Ser Asn His Gly Tyr Thr Ile Gly Ile His
    210                 215                 220
Ala Pro Gly Arg Cys Ser Cys Trp Tyr Asp Pro Thr Cys Leu Gly Gly
225                 230                 235                 240
Asp Ser Gly Thr Glu Pro Tyr Leu Val Thr His His Leu Leu Leu Ala
                245                 250                 255
His Ala Ala Ala Val Lys Leu Tyr Arg Glu Lys Tyr Gln Ala Ser Gln
                260                 265                 270
Asn Gly Val Ile Gly Ile Thr Ile Val Ser His Trp Phe Glu Pro Ala
            275                 280                 285
Ser Glu Ser Gln Gln Asp Lys Asp Ala Ala Ser Arg Ala Leu Asp Phe
    290                 295                 300
Met Tyr Gly Trp Phe Met Glu Pro Leu Thr Arg Gly Asp Tyr Pro Gln
305                 310                 315                 320
Thr Met Arg Ser Ile Val Gly Ser Arg Leu Pro Asn Phe Thr Glu Glu
                325                 330                 335
Gln Ser Lys Ser Leu Asn Gly Ser Tyr Asp Tyr Ile Gly Val Asn Tyr
                340                 345                 350
Tyr Ser Ala Arg Tyr Ala Ser Ala Tyr Thr Asn Asn Tyr Ser Val Pro
            355                 360                 365
Thr Pro Pro Ser Tyr Ala Thr Asp Ala Tyr Val Asn Val Thr Thr Thr
        370                 375                 380
Asp Leu Asn Gly Val Pro Ile Gly Pro Gln Ala Ala Ser Asp Trp Leu
385                 390                 395                 400
Tyr Val Tyr Pro Lys Gly Leu Tyr Asp Leu Val Leu Tyr Thr Lys Glu
                405                 410                 415
Lys Tyr Asn Asp Pro Val Met Tyr Ile Thr Glu Asn Gly Met Asp Glu
                420                 425                 430
Phe Asn Asn Pro Lys Leu Ser Leu Glu Glu Ala Leu Asp Asp Ala Asn
            435                 440                 445
Arg Ile Asp Tyr Tyr Arg His Leu Cys Tyr Leu Gln Ala Ala Ile
450                 455                 460
Lys Glu Gly Ala Asn Val Gln Gly Tyr Phe Ala Trp Ser Leu Leu Asp
465                 470                 475                 480
Asn Phe Glu Trp Ser Glu Gly Tyr Thr Val Arg Phe Gly Ile Asn Tyr
                485                 490                 495
Ile Asp Tyr Asp Asn Gly Leu Glu Arg His Ser Lys Leu Ser Thr His
                500                 505                 510
Trp Phe Lys Ser Phe Leu Lys Arg Ser Ser Ile Ser Lys Lys Ile
        515                 520                 525
Arg Arg Cys Gly Asn Asn Ala Lys Ala Thr Lys Phe Val Tyr Gln
    530                 535                 540
Met
545

<210> SEQ ID NO 5
<211> LENGTH: 1260
```

<212> TYPE: DNA
<213> ORGANISM: Prunus serotina

<400> SEQUENCE: 5

```
gataccgtgc gaaaggtctt cttggccctt ggagattgac acctaatcag aattttgata      60
aagttaaatg tatctaaaaa gtaatccctt ttcttttctt ttttcatcta taatagcaaa     120
cgaataaata ctatagacac agacctaaat atttgaagca catgtaacaa cagggcgcag     180
ccaaacgttt tcttcaacat attagttttt tcaattgtgt caaataagtc ggtatgaaag     240
aaaattctga gataaagatt ggtgcagcat aaatggactt tgaaaaaaa aaaaaattga     300
tccccctct ctaggtcttg gtgtcgaaag ccataaaaat tgatccccc ctcttttccc       360
tataactccc cttcccccct ctttaggttt tttaaagtta acagagatc acagagtgga     420
atcaccttct ctttattggg gcttggggtc ggatggatag gtgagggagt aggcgggtgc     480
gggtgaagct ggccgtgggg tttaagctac tttcttttc attttaaaat atgatttcta     540
ttacttgcac tttattattt tttgccaaag gtacttacac attattctat agtaaaagtt     600
gtccaaggcc cgtatgtaca tgagaggacg tgttgagagt agatattatg ttaagtccca     660
tatatacgtg agagggcatg ttgaaagtag atattatgtt aagttttgta tatacgtgag     720
aggatatgtt gagagtaaat attatgttaa gtctgttttt tttaaatga agtaatttgt     780
ttttagcaat taacaccaat tgatggaaat aggagagaaa acattaatgg agaaggatgc     840
aattagatta tctttccaaa accaaaggtt agggcacggg agcaaaacca gactctgaag     900
gtagtcccag tgggatcttt ggattgcttt tctataaagt agtatataaa gaaggatctt     960
tgggttactt gtctgatatt tttccgaaac aacccaccaa cattttact  atatgcatgc    1020
aggaccctac ttttctctgt ctgtacccat actttagctt cttctttttt tgtggttatc    1080
cgtactttag ttttaaggcc cgcttggctt tacaaaaaag aaagcaaaaa agacataaaa    1140
acttctctga tttattattt tcaggtgcag aagttacgta ctccctctat ataaagccca    1200
tgcaatatag caggaagagc aaacctagct cgatcaccaa aaaccctcct ctcagccatg    1260
```

<210> SEQ ID NO 6
<211> LENGTH: 862
<212> TYPE: DNA
<213> ORGANISM: Prunus serotina

<400> SEQUENCE: 6

```
tggggtgctt acacccacaa tcatccaggt ctacttattt tctccaaatc ctttatggt       60
ttcaactagt cagtgcccctt tgctctcaca attaagtcca catatgtgga ctacagtaat    120
taaacatatg gttttcaatg tctaaacaag ccaatacttc atggatttga gttatgcatg    180
gcataccgtt ctgttttaag tgttattaaa gtgcctgcaa ggaattctta caaggataca    240
attctatact aataccaata caagataaca taacaaaata ctaattcgct ctgacatcaa    300
tggcacacaa tgaggtgaca gtttccgag aaagttagag aaaatgttac ttgcattctc     360
caatttaata tctaaatagc taaattactt tgtgctttta attactaata gtcatgtaat     420
atgtatattt ggtctacaga catacacgca cacactagtt tacatgatct gatttcccaa     480
acttatgct taaataaaaa taatctttgg ttaattgcga gagaaatttg ttttgagcaa      540
ttaatgccaa ttgatggaga taggagagaa acattaatg gagaagggtg caattagatt     600
atctttccaa aaccagaggt tagggcacgg gagcaaaacc agactctgaa ggtgatccca     660
atggaatctt tggattgctt ttccatactt tagctttaaa gccctgctt ggctttacaa      720
```

```
aaaagaaagc aaaaagaaa gcaaatgct tttgatttat tattttcacg tgtagaagtt      780
atgtactcct tctatataaa tcccatgcaa tatagcagga agagcacacc tagctcgatc      840
ataaaaaatc ctccactgag cc                                              862
```

```
<210> SEQ ID NO 7
<211> LENGTH: 26
<212> TYPE: DNA
<213> ORGANISM: Artificial Sequence
<220> FEATURE:
<223> OTHER INFORMATION: Artificial Sequence

<400> SEQUENCE: 7
gtatcgaaat gggtcctgtt gagagt                                           26

<210> SEQ ID NO 8
<211> LENGTH: 26
<212> TYPE: DNA
<213> ORGANISM: Artificial Sequence
<220> FEATURE:
<223> OTHER INFORMATION: Artificial sequence

<400> SEQUENCE: 8
atatgtcccg gcagcattgg tatttg                                           26

<210> SEQ ID NO 9
<211> LENGTH: 21
<212> TYPE: DNA
<213> ORGANISM: Artificial Sequence
<220> FEATURE:
<223> OTHER INFORMATION: Artificial sequence

<400> SEQUENCE: 9
accgtgcgaa aggtcttctt g                                                21

<210> SEQ ID NO 10
<211> LENGTH: 21
<212> TYPE: DNA
<213> ORGANISM: Artificial Sequence
<220> FEATURE:
<223> OTHER INFORMATION: Artificial sequence

<400> SEQUENCE: 10
atgccatggc tgagaggagg g                                                21

<210> SEQ ID NO 11
<211> LENGTH: 25
<212> TYPE: DNA
<213> ORGANISM: Artificial Sequence
<220> FEATURE:
<223> OTHER INFORMATION: Artificial sequence

<400> SEQUENCE: 11
ggggtgctta cacccacaat catcc                                            25

<210> SEQ ID NO 12
<211> LENGTH: 22
<212> TYPE: DNA
<213> ORGANISM: Artificial Sequence
<220> FEATURE:
<223> OTHER INFORMATION: Artificial sequence

<400> SEQUENCE: 12
gcaatgccat ggctcagtgg ag                                               22
```

-continued

```
<210> SEQ ID NO 13
<211> LENGTH: 862
<212> TYPE: DNA
<213> ORGANISM: Prunus serotina

<400> SEQUENCE: 13
tggggtgctt acacccacaa tcatccaggt ctacttattt tctccaaatc cttttatggt      60
ttcaactagt cagtgccctt tgctctcaca attaagtcca catatgtgga ctacagtaat     120
taaacatatg gttttcaatg tctaaacaag ccaatacttc atggatttga gttatgcatg     180
gcataccgtt ctgttttaag tgttattaaa gtgcctgcaa ggaattctta caaggataca     240
attctatact aataccaata caagataaca taacaaaata ctaattcgct ctgacatcaa     300
tggcacacaa tgaggtgaca agtttccgag aaagttagag aaaatgttac ttgcattctc     360
caatttaata tctaaatagc taaattactt tgtgcttta attactaata gtcatgtaat     420
atgtatattt ggtctacaga catacacgca cacactagtt tacatgatct gatttcccaa     480
actttatgct taaataaaaa taatctttgg ttaattgcga gagaaatttg ttttgagcaa     540
ttaatgccaa ttgatggaga taggagagaa aacattaatg gagaagggtg caattagatt     600
atctttccaa aaccagaggt tagggcacgg gagcaaaacc agactctgaa ggtgatccca     660
atggaatctt tggattgctt ttccatactt tagctttaaa gcccctgctt ggctttacaa     720
aaaagaaagc aaaaaagaaa gcaaaatgct tttgatttat tattttcacg tgtagaagtt     780
atgtactcct tctatataaa tcccatgcaa tatagcagga agagcacacc tagctcgatc     840
ataaaaaatc ctccactgag cc                                              862
```